US006905673B2

United States Patent
Rajaiah et al.

(10) Patent No.: US 6,905,673 B2
(45) Date of Patent: Jun. 14, 2005

(54) ORAL CARE KITS AND COMPOSITIONS

(75) Inventors: Jayanth Rajaiah, Loveland, OH (US); Lisa Catron Ernst, Cincinnati, OH (US); Ann Maria Case, Cincinnati, OH (US); Thinh Nguyen Ha, Cincinnati, OH (US); William Michael Glandorf, Mason, OH (US); Christopher Robert Mayer, Cincinnati, OH (US)

(73) Assignee: The Procter & Gamble Co, Cincinnati, OH (US)

( * ) Notice: Subject to any disclaimer, the term of this patent is extended or adjusted under 35 U.S.C. 154(b) by 249 days.

(21) Appl. No.: 10/242,012

(22) Filed: Sep. 12, 2002

(65) Prior Publication Data

US 2003/0082113 A1 May 1, 2003

Related U.S. Application Data

(63) Continuation of application No. 10/084,898, filed on Feb. 28, 2002, now Pat. No. 6,509,007.
(60) Provisional application No. 60/276,979, filed on Mar. 19, 2001, and provisional application No. 60/276,978, filed on Mar. 19, 2001.

(51) Int. Cl.⁷ .............................. A61K 7/16; A61K 7/18
(52) U.S. Cl. .......................... 424/49; 424/52; 424/401; 433/215; 433/216; 433/217.1; 433/228.1; 523/109

(58) Field of Search .............................. 424/49–58, 401; 433/215, 216, 217.1, 228.1; 523/109

(56) References Cited

U.S. PATENT DOCUMENTS

| | | |
|---|---|---|
| 4,554,154 A | 11/1985 | White |
| 4,948,850 A | 8/1990 | Hasenbein et al. |
| 5,114,718 A | 5/1992 | Damani |
| 5,185,386 A | 2/1993 | Cohen et al. |
| 5,496,541 A | 3/1996 | Cutler |
| 5,562,862 A | 10/1996 | Berzansky, Jr. et al. |
| 5,880,172 A | 3/1999 | Rajaiah et al. |
| 5,900,230 A | 5/1999 | Cutler |
| 6,054,484 A | 4/2000 | Sekine et al. |

Primary Examiner—Frederick Krass
(74) Attorney, Agent, or Firm—Betty J. Zea; Angela K. Haughey

(57) ABSTRACT

An oral care composition comprises polybutene with a molecular weight of about 300 to about 3000 and an oral care active. The oral care composition may further comprise an oral care carrier. Kits comprising polybutene, a container and instructions for use or an applicator for applying the composition directly to the tooth surfaces are also disclosed. The polybutene component of the kits can further comprise an oral care active or an oral care carrier.

34 Claims, No Drawings

ORAL CARE KITS AND COMPOSITIONS

CROSS-REFERENCE TO RELATED APPLICATIONS

This application is a continuation of U.S. Ser. No. 10/084,898, filed Feb. 28, 2002 now U.S. Pat. No. 6,509,007, which claims the benefit of U.S. Provisional Application 60/276,979, filed Mar. 19, 2001 and U.S. Provisional Application 60/276,978, also filed Mar. 19, 2001.

FIELD OF THE INVENTION

The present invention relates to oral care compositions and oral care kits providing prolonged release of therapeutic, prophylactic and cosmetic actives to the oral cavity and inhibiting the buildup of plaque and other debris and on the teeth.

BACKGROUND OF THE INVENTION

Oral care products by which various oral care actives can be delivered to the hard surface of the teeth have been previously known. Examples of such oral care products include: brushing aids such as dentifrice products for delivery of anti-caries actives like fluoride; and mouthwashes containing breath fresheners or antibacterial actives. It is well known that oral care products can provide both therapeutic and cosmetic benefits to consumers. However, such conventional oral care products typically do not maintain actives in the oral cavity long enough to optimally enhance or prolong the therapeutic, prophylactic and/or cosmetic benefits provided by the actives.

Polybutene is recognized as a component of denture adhesives and as a gum base. U.S. Pat. No. 5,880,172, issued Mar. 3, 1999, to Rajaiah, et al., discloses a self-supporting denture adhesive that is peelable for easy removal, which incorporates polybutene as an optional ingredient. U.S. Pat. No. 5,496,541, issued Mar. 5, 1996, to Cutler, relates to a dentifrice chewing gum and teaches the use of polybutene as an optional gum base. Such known applications often employ higher molecular weight polybutene in order to achieve the desired result.

In the present invention lower molecular weight polybutene is incorporated in oral care kits and compositions to provide a protective coating on the teeth. Good, uniform coating of the teeth is achieved because the lower molecular weight polybutene is a flowable liquid. The use of lower molecular weight polybutene in the polybutene-containing component of the oral care kits and compositions provides sufficient substantivity to provide sustained release of an oral care active, without causing unwanted coating or buildup on the oral mucosa.

The present invention provides oral care kits and compositions that effectively coat and protect the teeth from buildup of plaque and other debris, thereby inhibiting or preventing gingivitis, caries and staining of the teeth. This coating also provides a slick, smooth feel to the hard surfaces of the oral cavity which consumers view as an indicator of clean teeth. The present invention can also be used to deliver an oral care active to the teeth and oral cavity through incorporation of said active within the polybutene-containing component.

SUMMARY OF THE INVENTION

The present invention relates to oral care compositions comprising polybutene with a molecular weight of about 300 to about 3000 and an oral care active. An oral care composition comprising polybutene with a molecular weight of about 300 to about 3000 and an oral care carrier is also disclosed. In one embodiment a composition comprising polybutene with a molecular weight of about 300 to about 3000, an oral care carrier, and an oral care active is used to deliver the therapeutic and cosmetic benefits directly to the teeth and oral cavity. The present invention also relates to an oral care kit comprising polybutene with a molecular weight of about 300 to about 3000, a container, and instructions for the use of the kit. Another oral care kit of the present invention comprises polybutene with a molecular weight of about 300 to about 3000 and an applicator for applying the composition to the teeth, wherein the applicator is not a strip means.

The oral care actives incorporated within the composition, and optionally included within the oral care kits, can be selected from the group consisting of anti-calculus or anti-tartar agents, fluoride ion sources, stannous ion sources, whitening agents, anti-microbial and anti-plaque agents, anti-inflammatory agents, nutrients, antioxidants, anti-viral agents, anti-fungal agents, analgesic and anesthetic agents, H-2 antagonists, fragrances and sensates, components other than polybutene which impart a clean feel to the teeth, pigments and colorants, and mixtures thereof. Oral care carriers that are suitable for use in the present invention include, but are not limited to, abrasive polishing materials, alkali metal bicarbonate salts, acidic compounds, buffering agents, polyoxyethylene, thickeners, humectants, water, surfactants, opacifiers, flavorants, sweeteners and xylitol. When desired a viscosity modifier may optionally be incorporated in the present invention. The compositions are not self-supporting.

DETAILED DESCRIPTION OF THE INVENTION

Definitions

The term "teeth", as used herein, is meant to include natural teeth, and any other hard surfaces, such as crowns, caps, fillings, bridges, dental implants, and the like, that are permanently fixed within the oral cavity and cleansed in situ within the oral cavity.

The oral care composition may be a single-phase oral care composition or may be a combination of two or more oral compositions delivered in various phases. The oral composition is a product that, in the ordinary course of usage, is not intentionally swallowed for purposes of systemic administration of particular therapeutic agents, but rather, is retained in the oral cavity for a time sufficient to contact substantially all of the dental surfaces and/or oral tissues for purposes of oral activity.

The term "container" as described herein, means a jar, cup, can, tube, aerosol can, tub, pump, bottle or any other liquid holding or dispensing means.

The term "dentifrice", as used herein, means paste, gel, or liquid formulations used to clean the teeth, unless otherwise specified. The dentifrice composition may be in any desired form, such as deep striped, surface striped, multi-layered, having the gel surrounding the paste, or any combination thereof. The dentifrice composition may be contained in physically separated compartments of a dispenser and dispensed side-by-side.

The term "oral care carrier" as used herein means any safe and effective materials for use in the compositions of the present invention. Such materials include polyoxyethylene, acidic compounds, buffering agents, abrasive polishing materials, alkali metal bicarbonate salts, thickeners, humectants, water, surfactants, opacifiers such as titanium dioxide, flavorants, sweetening agents, xylitol, coloring agents, and mixtures thereof.

By "safe and effective amount", as used herein, is meant an amount of an agent (e.g., anti-calculus agent) high enough to significantly improve the condition to be treated, but low enough to avoid serious side effects (at a reasonable benefit/risk ratio), within the scope of sound medical/dental judgment. The safe and effective amount of an agent (e.g., anti-calculus agent) may vary with the particular condition being treated, the age and physical condition of the patient being treated, the severity of the condition, the duration of treatment, the nature of concurrent therapy, the specific form of the source employed, and the particular vehicle from which the agent is applied.

The term "mucoadhesive" or "bioadhesive" as used herein refers to the phenomenon where a natural or synthetic substance applied to a wet mucosal epithelium adheres, usually creating a new interface, to the mucous layer. (*CRC Critical Review in Ther. Drug Carrier*, Vol.5, Issue 1, p.21 (1988)). Generally, mucoadhesion can be achieved via physical or chemical processes, or both. This mechanism is described in *Journal of Controlled Release*, Vol.2, p257 (1982) and *Journal of Controlled Release*, Vol.18 (1992) p. 249. The above references are incorporated by reference herein in their entirety.

The term "non-self supporting" is used to describe a composition that lacks integrity and strength. In the instant case, this means that the composition is unable to be detached as one solid piece from the teeth even after several hours of use in the mouth. The composition cannot be cut and formed into definite shapes, such as a sheet or cone, which maintain their initial dimensions.

"Tartar" and "calculus" are used interchangeably and refer to mineralized dental plaque biofilms.

The term "unit dose form" refers to physically discrete units suitable as unitary dosages for human subjects and other mammals, each containing a predetermined quantity of active material calculated to produce the desired therapeutic effect.

The term "viscosity" as used herein refers to kinematic viscosity, measured using the standard test method for Kinematic Viscosity of Transparent and Opaque Liquids (the Calculation of Dynamic Viscosity), ASTM D-445. As reported, viscosity is measured at 99° C. (210° F.) unless otherwise indicated. A sample is placed in a U-shaped "Cannon-Fenske" type viscometer (for transparent liquids) tube and submerged into a constant temperature bath. Flow is timed between two marks on the tube and viscosity is determined by simple calculations dependent on time and a standard factor supplied by the tube manufacturer.

"Molecular weight", as referred to herein, is reported as a number average, determined using gel permeation chromatography. The number average molecular weight, or arithmetic mean, is a function of the number of molecules in a given mass of polymer. It is represented by the formula:

$$M_n = \frac{\sum N_i M_i}{\sum N_i} = \sum n_i M_i$$

where $N_i$, represents the number of molecules present for a given molecular weight, $M_i$ and $n_i = N_i / \sum N_i$ is the number fraction of molecular weight, $M_i$.

Percentages and ratios herein are by weight of total composition, unless otherwise indicated.

Polybutene

Polybutene is a viscous copolymer of isobutylene and butene monomers. "Polybutene", as used herein, refers to both hydrogenated (CAS #68937-10-0) and unhydrogenated (CAS #9003-29-6) forms of the polymer. Polybutene is a viscous, colorless, non-drying, liquid polymer. Polybutenes range from a flowable liquid to a near semi-solid state. Polybutenes are clear, odorless, chemically stable, resistant to oxidation by light and heat, non-toxic and non-hazardous.

The oral care compositions and kits of the present invention comprise polybutene of a lower molecular weight, from about 300 to about 3000, in another embodiment from about 500 to about 2200, and in yet another embodiment from about 750 to about 1500. The viscosity of the polybutene disclosed herein, ranges from about 30 cSt (centi Stoke) measured at 38° C. to about 4,500 cSt measured at 99° C., in another embodiment from about 200 cSt measured at 38° C. to about 3,500 cSt measured at 99° C., and in another embodiment from about 75 cSt measured at 99° C. to about 700 cSt measured at 99° C. Polybutene comprises from about 0.01% to about 100%, by weight of the polybutene-containing component, in another embodiment from about 1% to about 100%, by weight of the polybutene-containing component, in yet another embodiment from about 50% to about 100%, by weight of the polybutene-containing component.

The lower molecular weight polybutene of the present invention does not exhibit elastomeric properties. Elastomers are amorphous polymers that have the ability to stretch out and spring back to their original shapes. Such elastomeric polymers must have a modest amount of cross-linking to prevent the polymeric chains from slipping over one another, and the chains must have an irregular shape to prevent the formation of crystalline regions within the polymeric chains. Synthetic elastomers, are described in more detail in Kirk-Othmer, *Encyclopedia of Chemical Technology*, Fourth Edition, Volume 8, Wiley-Interscience Publishers (1996), pages 934–955, incorporated herein by reference in its entirety, including all references incorporated into Kirk-Othmer. The polybutene utilized in the present invention is not cross-linked and does not exhibit rubbery or elastic behavior. When subjected to a stretching or bending force, the polybutene herein does not regain its original shape upon the removal of the force.

Lower molecular weight polybutene (Molecular Weight= 300–3000), which is a flowable liquid known for its adhesive properties, is actually non-mucoadhesive. That is, the polybutene, while displaying excellent adhesion properties on the hard surfaces of the oral cavity, will not significantly adhere to the mucosa or wet, soft tissue of the mouth. In fact, polybutene is extremely substantive when applied to the teeth, making it suitable for once daily application and treatment. High retention of the polybutene is achieved, even when thorough brushing has occurred. Thus, the polybutene, once applied to the tooth surface, is long lasting, and rinse resistant, which allows for sustained release of certain optional oral care actives. Importantly, the compositions of the present invention are not self-supporting before, during, or after application to the teeth. Once applied to the teeth, the polybutene has a very smooth, slick texture, perceived by the consumer as a desirable, clean feeling. The polybutene acts as a lubricant and reduces the friction normally generated when the tongue slides over the teeth.

Suitable polybutenes for use herein include, but are not limited to: Indopol L-14, Molecular Weight ('MW")=370; Indopol L-50, MW=455; Indopol L-65, MW=435; Indopol L-100, MW=510, H-15, MW=600; H-25, MW=670; H-35, MW=725; H-40, MW=750; H-50, MW=815; H-35, MW=940; H-300, MW=1330; H-1500, MW=2145; H-1900, MW=2270; Panalane L-14E, MW=370; Panalane H-300E, MW=1330; all trade names of BP Amoco Chemicals (Chicago, Ill.). Other suitable grades of polybutene include Parapol 450, MW=420; Parapol 700, MW=700; Parapol 950, MW=950; Parapol 1300, MW=1300; and Parapol 2500, MW=2700; all trade names of ExxonMobil Corporation.

Oral Care Actives

The oral care kits and compositions of the present invention may contain one or more oral care actives in unit dose form where, upon directed use, the benefit sought by the user is promoted without detriment to the oral surface to which it is applied. Examples of the oral conditions these actives address include, but are not limited to, appearance and structural changes to teeth, treatment and prevention of plaque, calculus, cavities, inflamed and/or bleeding gums, gingivitis, fungal infections such as candida, mucosal wounds, lesions, ulcers, aphthous ulcers, cold sores, tooth abscesses, and the elimination of mouth malodor resulting from the conditions above and other causes such as microbial proliferation.

Suitable oral care actives include any material that is generally considered safe for use in the oral cavity and that provides changes to the overall appearance and/or health of the oral cavity. When present, the level of oral care active in the oral care kits and compositions of the present invention is generally, unless otherwise noted, from about 0.001% to about 90%, in one embodiment from about 0.01% to about 50%, in another embodiment from about 0.1% to about 30%, by weight of the composition. Where the oral care actives are in particulate form, a suitable particle size for use in the present invention is from about 0.01 microns to about 1000 microns, in one embodiment from about 0.1 microns to 500 microns, in another embodiment from about 1 to about 100 microns. The oral care kits and compositions of the present invention may include many of the oral care actives previously disclosed in the art. The following is a non-limiting list of oral care actives that may be used in the present invention.

The present compositions may comprise at least one anti-calculus (i.e. anti-tartar) agent, present at a level from about 0.001% to about 50%, by weight of the composition, in another embodiment from about 0.01% to about 25%, and in yet another embodiment from about 0.1 to about 15%. The anti-calculus agent should be essentially compatible with the other components of the invention. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos ($n \approx 6$), Hexaphos ($n \approx 13$), and Glass H ($n \approx 21$, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Fluoride ion sources are known for use in oral care compositions as anti-caries agents for teeth and may optionally be incorporated within the present invention. Application of fluoride ions to the dental enamel of natural teeth serves to protect those teeth against decay. A wide variety of fluoride ion-yielding materials can be employed as sources of soluble fluoride in the instant compositions. Examples of suitable fluoride ion-yielding materials are found in Briner, et al., U.S. Pat. No. 3,535,421 and Widder, et al., U.S. Pat. No. 3,678,154. Preferred fluoride ion sources for use herein include sodium fluoride, potassium fluoride, stannous fluoride, mono fluoro phosphate (MFP), and ammonium fluoride. In one embodiment sodium fluoride is the fluoride ion source. The instant invention provides from about 5 ppm to 10,000 ppm, in one embodiment from about 100 to 3000 ppm, of fluoride ions in the total composition.

The compositions of the present invention may include a stannous ion source. The stannous ions may be provided from stannous fluoride and/or other stannous salts. Stannous fluoride has been found to help in the reduction of gingivitis, plaque, sensitivity, and in improved breath benefits. The stannous ions provided in an oral composition will provide efficacy to a subject using the composition. Although efficacy could include benefits other than the reduction in gingivitis, efficacy is defined as a noticeable amount of reduction in in situ plaque metabolism. Formulations providing such efficacy typically include stannous levels provided by stannous fluoride and/or other stannous salts ranging from about 3,000 ppm to about 15,000 ppm stannous ions in the total composition. Below about 3,000 ppm stannous the efficacy of the stannous is insufficient. The stannous ion is present in a level of from about 4,000 ppm to about 12,000 ppm, in another embodiment from about 5,000 ppm to about 10,000 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride in another embodiment, stannous chloride dihydrate. The combined stannous salts may be present in an amount of from about 0.01% to about 11%, by weight of the compositions. The stannous salts may typically be present in an amount of from about 0.1% to about 7%, in one embodiment from about 1% to about 5%, and in yet another embodiment from about 1.5% to about 3%, by weight of the composition.

Anti-microbial agents can also be present in the compositions of the present invention. Such agents may include, but are not limited to: 5-chloro-2-(2,4-dichlorophenoxy)-phenol, commonly referred to as Triclosan, and described in *The Merck Index*, 11th ed. (1989), pp. 1529 (entry no. 9573) in U.S. Pat. No. 3,506,720, and in European Pat. Application No. 0,251,591 of Beecham Group, PLC,; 8-hydroxyquinoline and its salts; copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, preferably magnesium monopotassium phthalate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; iodine; sulfonamides; bisbiguanides; phenolics; delmopinol, octapinol, and other piperidino derivatives; nicin preparations; zinc/stannous ion agents; nystatin; grapefruit extracts; apple extracts; thyme oil; thymol; antibiotics such as augmentin, amoxicillin, tetracycline, doxycycline, minocycline, metronidazole, neomycin, kanamycin, and clindamycin; analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite; and mixtures of all of the above.

The compositions of the present invention may include an anti-plaque agent such as stannous salts, copper salts, strontium salts, magnesium salts or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol is generally present in a level of from about 0.001% to about 25%, in one embodiment from about 0.01% to about 5% and in another embodiment from about 0.1% to about 1.5% by weight of the composition.

Anti-inflammatory agents can also be present in the oral care kits and compositions of the present invention. Such agents may include, but are not limited to, non-steroidal anti-inflammatory agents oxicams, salicylates, propoionic acids, acetic acids and fenamates. Such NSAIDs include but are not limited to Ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluccinolone, and hydrocortisone.

Nutrients may improve the condition of the oral cavity and can be included in the compositions of the present invention. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in *Drug Facts and Comparisons* (loose leaf drug information service), Wolters Kluer Company, St. Louis, Mo., © 1997, pps. 3–17 and 54–57.

A whitening agent may be included as an oral care active in the present invention. Such substances are selected from the group consisting of peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional bleaching substances may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine respectively that the molecule is capable of providing to bleach the stain. This level is generally used in compositions of the present invention at levels from about 0.1% to about 35%, in one embodiment from about 1% to about 25% and in another embodiment from about 5% to about 10% of the composition.

Antioxidants are recognized as useful in oral care compositions. Antioxidants are disclosed in texts such as Cadenas and Packer, *The Handbook of Antioxidants*, © 1996 by Marcel Dekker, Inc. Antioxidants that may be included in the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

Antiviral actives useful in the present invention include any known actives that are routinely used to treat viral infections. Such antiviral actives include, but are not limited to: phosphonoformic acid; cyosine derivatives; purine anaglogues, such as adenosine, guanosine and inosine analogues; pyrimidine bases, such as citidine and thymidine; amantadines; rimantadine HCl; ribavirin; zanamivir; oseltamivir phosphate; trifluridine; heterocyclic dyes; acyclovir; famciclovir; valacyclovir, cidofovir; ganciclovir; levimisole; idoxuridine; lipophilic β-ketones; and thiosemicarbazones. These antiviral actives are described in *Drug Facts and Comparisons* (loose-leaf drug information service), Wolters Kluwer Company, St. Louis, Mo., ©2001, pp. 1400–1423 (b), and in *Kirk-Othmer, Encyclopedia of Chemical Technology*, Fourth Edition, Volume 3, Wiley-Interscience Publishers (1992), pp. 576–607, both incorporated herein by reference in their entirety. Specific examples include antiviral actives disclosed in U.S. Pat. No. 5,747,070, to Majeti, incorporated herein by reference in its entirety. Said patent discloses the use of stannous salts to control viruses. Stannous salts are described in more detail above. While stannous fluoride may be used as an antiviral agent, it is typically used only in combination with another stannous halide or one or more stannous carboxylates or another therapeutic agent.

Anti-fungal agents can also be included in the oral care kits and compositions of the present invention. Anti-fungals are agents that destroy or inhibit the growth of fungi. Anti-fungal agents useful in the present invention are those drugs for systemic mycoses or drugs for mucocutaneuos infections. Suitable antifungals include but are not limited to nystatin; miconazole; econazole nitrate; clotrimazole; and flucytosine. In one embodiment the antifungal agent is nystatin.

Anti-pain or desensitizing agents can also be included in the oral care kits and compositions of the present invention. Analgesics are agents that relieve pain by acting centrally to elevate pain threshold without disturbing consciousness or altering other sensory modalities. Such agents may include, but are not limited to, strontium chloride, potassium nitrate, sodium fluoride, sodium nitrate, acetanilide, phenacetin, acertophan, thiorphan, spiradoline, aspirin, codeine, thebaine, levorphenol, hydromorphone, oxymorphone, phenazocine, fentanyl, buprenorphine, butaphanol, nalbuphine, pentazocine, natural herbs such as gall nut, Asarum, Cubebin, Galanga, scutellaria, Liangmianzhen, Baizhi, etc. Anesthetic agents, or topical analgesics, such as acetaminophen, sodium salicylate, trolamine salicylate, lidocaine and benzocaine may also be present. These analgesic actives are described in detail in *Kirk-Othmer, Encyclopedia of Chemical Technology*, Fourth Edition, Volume 2, Wiley-Interscience Publishers (1992), pp. 729–737, incorporated herein by reference in its entirety.

Histamine-2 (H-2 or H2) receptor antagonist compounds (H-2 antagonists) may be used in the compositions of the present invention. As used herein, selective H-2 antagonists are compounds that block H-2 receptors, but do not have meaningful activity in blocking histamine-1 (H-1 or H1) receptors. Selective H-2 antagonists stimulate the contraction of smooth muscle from various organs, such as the gut and bronchi; this effect can be suppressed by low concentrations of mepyramine—a typical antihistaminic drug. The H-2 antagonists useful in the present invention are those that blockade the receptors involved in mepyramine-insensitive, non-H-1 (H-2), histamine responses and do not blockade the receptors involved in mepyramine-sensitive histamine responses. Selective H-2 antagonists include compounds meeting the above criteria which are disclosed in U.S. Pat. Nos. 5,294,433 and 5,364,616 both to Singer, et al., and assigned to The Procter & Gamble Company, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HIB-408. Related suitable H-2 antagonists include burimamide and metiamide.

The present invention may also include one or more components that provide fragrance, and/or sensate benefit (warming or cooling agents). Suitable components include menthol, menthyl lactate, wintergreen oil, peppermint oil, spearmint oil, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, cinnamon, thymol, linalool, benzaldehyde, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10, manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al. WS-3 and other agents are described in U.S. Pat. No. 4,136,163, Watson, et al. The disclosures of both are herein incorporated by reference in their entirety.

Pigments may be added to the compositions herein to more precisely indicate the locations at which the composition has actually been in contact. Additionally, these substances may be suitable for modifying the color of the denture to satisfy the consumer. These substances comprise particles that when applied on the tooth surface modify that surface in terms of absorption and, or reflection of light. Such particles provide an appearance benefit when a film containing such particles is applied over the surfaces of the denture. Pigments, dyes, colorants and lakes may also be added to modify the appearance of the compositions herein to render the product more acceptable to the consumer. Appropriate pigment levels are selected for the particular impact that is desirable to the consumer. For example, for dentures that are particularly dark or stained one would typically use pigments in sufficient amounts to lighten the teeth. On the other hand, where individual teeth or spots on the teeth are lighter than other teeth, pigments to darken the denture may be useful. The levels of pigments and colorants may be in the range of about 0.001% to about 20%, in one embodiment from about 0.01% to about 15% and in another embodiment from about 0.1 % to about 10% by total weight of the composition.

Pigments and colorants include inorganic white pigments, inorganic colored pigments, pearling agents, filler powders and the like; see Japanese Published Pat. Application Kokai No. 9 [1997]-100215, published Apr. 15, 1997, incorporated herein by reference. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. In one embodiment the pigments and colorants are those selected from the group consisting of titianium dioxide, bismuth oxychloride, zinc oxide, Opatint D&C Red 27, CI 16185:1 Acid 27 Lake E123, CI14720:1 Carmosoisine Aluminum Lake E122, Red 7 Lake, or Red 30 Lake, and mixtures thereof.

Additional actives suitable for use in the present invention may include, but are not limited to, insulin, steroids, herbal and other plant derived remedies, and anti-neoplastics. Additionally, anti-gingivitis or gum care agents known in the art may also be included. Components, other than polybutene, which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single composition to provide combined effectiveness.

Oral Care Carriers

Where one or more oral care carriers is incorporated within the oral care compositions of the present invention, such materials are selected from those well known in the art and are readily chosen by one skilled in the art based on the physical and aesthetic properties desired for the compositions being prepared. The resulting oral care composition may take the form of a dentifrice, mouth rinse, mouth spray, topical oral gel, a teeth whitening gel or the like. These oral care carriers may be included at levels that do not interfere with or prohibit surface conditioning. Oral care carriers typically comprise from about 10% to about 99%, in one embodiment from about 45% to about 98%, in yet another embodiment from about 75% to about 95%, by total weight of the oral composition. In one embodiment the polybutene component of the composition, which may also contain an active, and the oral care carrier component are prepared separately and may then be combined into a single phase oral care product or the phases can be physically separated until the time of administration rendering a multi-phase oral care product.

An abrasive polishing material may be included as an oral care carrier in the oral compositions of the present invention. The abrasive polishing material contemplated for use in the present invention can be any material that does not excessively abrade dentin. The abrasive polishing material should be formulated in the oral composition so that it does not compromise the stability of any ingredients, such as stannous fluoride. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley, et al., in U.S. Pat. No. 3,070,510, incorporated herein by reference. Silica dental abrasives of various types may be selected for use because of their unique benefits of exceptional dental cleaning and polishing performance without unduly abrading tooth enamel or dentine. The abrasive can be precipitated silica or silica gels such as the silica xerogels described U.S. Pat. No. 3,538,230 to Pader, et al., and U.S. Pat. No. 3,862,307 to DiGiulio, both incorporated herein by reference. Preferred are the silica xerogels marketed under the trade name "Syloid" by the W.R. Grace & Company, Davison Chemical Division and the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in U.S. Pat. No. 4,340,583, to Wason, incorporated herein by reference. The abrasive in the toothpaste compositions described herein is generally present at a level of from about 6% to about 70% by weight of the composition. In one embodiment toothpastes contain from about 10% to about 50% of abrasive, by weight of the oral care component of the oral care compositions of the presenting invention. Mixtures of abrasives may also be used. The abrasive polishing materials herein, generally have an average particle size ranging between about 0.1 to about 30 microns, and in one embodiment from about 5 to about 15 microns.

The present invention may include an alkali metal bicarbonate salt as an oral care carrier. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.001% to about 50%, in one embodiment from about 0.01% to about 30%, in another embodiment from about 0.1% to about 20%, and in yet another embodiment from about 1% to about 18% of an alkali metal bicarbonate salt, by weight of the oral care carrier component of the oral care composition.

The oral care compositions may contain a buffering agent. Buffering agents, as used herein, refer to agents that can be used to adjust the pH of the compositions to a range of about pH 3 to about pH 10. An oral care composition containing a polymeric surface active agent will typically have a slurry pH of from about 4 to about 10, in one embodiment from about 4.5 to about 8, and in another embodiment from about 5 to about 7. The buffering agents include alkali metal hydroxides, carbonates, sesquicarbonates, borates, silicates, phosphates, iridazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents may be used at a level of from about 0.01% to about 30%, in one embodiment from about 0.1% to about 10%, and in another embodiment from about 1% to about 3%, by weight of the oral care carrier component of the oral care composition.

Water employed in the preparation of commercially suitable oral compositions should preferably be of low ion content and free of organic impurities. Water will generally comprise from about 5% to about 70%, and in one embodiment from about 10% to about 50%, by weight of the oral care carrier component of the oral care composition described herein. The polymeric surface active agent may require a lower level of water to be stable. Generally, the level of water is up to about 20%, in one embodiment from about 5% to about 14%, and in another embodiment from about 7% to about 12%, by weight of the oral care carrier component of the oral care composition. The amounts of water include the free water which is added plus that which is introduced with other materials, such as with sorbitol, silica, surfactant solutions, and/or color solutions.

The oral care compositions of the present invention may also comprise surfactants, commonly referred to as sudsing agents. Suitable surfactants are those that are reasonably stable and foam throughout a wide pH range. The surfactants are present at a level of from about 0.001% to about 12%, in one embodiment from about 0.01% to about 8%, and in another embodiment from about 0.1% to about 6%, by weight of the oral care carrier component of the oral care composition. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauryl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed in U.S. Pat. No. 3,959,458, to Agricola, et al., incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed in U.S. Pat. No. 4,051,234, Gieske, et al., incorporated herein by reference in its entirety.

The oral care carrier component of the present invention may incorporate an acidic compound. The acidic compound may be organic or inorganic. The acidic compound may be any material that will act as a proton donor capable of neutralizing bicarbonate. Acidic compounds suitable for use include carboxylic acids, phosphoric acids, alpha-hydroxy acids, sulfonic acids, and mixtures thereof. Specific acids include citric acid, malic acid, alginic acid, succinic acid, lactic acid, tartaric acid, glycolic acid, adipic acid, potassium bitartrate acid, acid sodium citrate, phosphoric acid, boric acid, and acid phosphate pyrophosphate salts, and mixtures thereof. In one embodiment citric acid is used, in another embodiment malic acid is used. Acid anhydrides and acid salts of the above acids may also be used. Suitable salts include mono or disodium salts of citric acid, mono sodium salts of malic acid, and mixtures thereof. The oral care carrier component of the oral care compositions may contain from about 0.01% to about 20%, in one embodiment from about 0.1% to about 15% and in another embodiment from about 1% to about 12% of an acidic compound, by total weight of the oral care component.

The present invention may include polyoxyethylene. The polyoxyethylene will increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be from about 600,000 to about 2,000,000 and in another embodiment from about 800,000 to about 1,000,000. "Polyox" is the trade name for the high molecular weight polyoxyethylene produced by Union Carbide. The polyoxyethylene may be present in an amount from about 0.1% to about 8%, in one embodiment from about 0.2% to about 5% and in another embodiment from about 0.3% to about 2% by weight of the oral care carrier component of the oral care compositions of the present invention.

Compositions of the present invention may contain some thickening material or binders to provide a desirable consistency. Suitable thickening agents include, without limitation carboxyvinyl polymers, carrageenan, hydroxyethyl cellulose, and water-soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.01% to about 15%, by weight of the oral care carrier component.

Another optional component of the compositions described herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, and other edible polyhydric alcohols. The humectant may comprise from about 0% to about 70%, and in one embodiment from about 15% to about 55%, by weight of the oral care carrier component of the oral care composition.

The present invention may also include xylitol. Xylitol is a sugar alcohol that is used as a sweetener and humectant. Xylitol may provide a therapeutic effect, such as an anti-bacterial or anti-caries effect. The present compositions may comprise xylitol at a level from about 0.01% to about 25%, in one embodiment from about 3% to about 15%, and in another embodiment from about 5% to about 12%, by weight of the total oral care carrier component. Alternatively, if xylitol is used as a sweetener, it may be present at a lower level, such as from about 0.005% to about 5%, by weight of the oral care component of the oral care compositions of the present invention.

Any other compatible oral care carrier that is known in the art may be incorporated in the oral care carrier component of the oral care compositions of the present invention. For example, titanium dioxide may be incorporated in the present invention as an opacifier. Certain oral care actives, described above, such as stannous fluoride and anti-microbial agents may be incorporated within the oral care carrier component of the oral care compositions, as these substances are also well known as oral care carriers.

The oral care kits and compositions may further comprise a viscosity modifier that inhibits settling and separation of components or controls settling in a manner that facilitates re-dispersion and may control flow properties. A viscosity modifier is particularly useful to keep oral care actives that are in particulate form suspended within the polybutene components of the present invention. Suitable viscosity modifiers herein include mineral oil, organo modified clays, petrolatum, silicas, and mixtures thereof. In one embodiment the viscosity modifier is silica. Where incorporated, the viscosity modifier is present in the polybutene component of the present invention at a level of from about 0.1% to about 30%, in one embodiment from about 0.5% to about 10%, and in another embodiment from about 1% to about 3% of the composition.

The compositions may optionally further comprise one or more flavorants. These flavoring agents can be chosen from synthetic flavoring liquid and/or oils derived from plants leaves, flowers, fruits and so forth, and combinations thereof. Representative flavoring liquids include: vanillin, sage, marjoram, parsley oil, spearmint oil, cinnamon oil, oil of wintergreen (methylsalicylate), peppermint oils clove oil, bay oil, anise oil, and eucalyptus oil. Also useful are artificial, natural or synthetic fruit flavors such as citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. Additionally, flavor adsorbed onto a hydrophilic matrix may be included, e.g. "spray-dried" flavors. Furthermore, encapsulated flavors may be included. The amount of flavorant employed is normally a matter of preference subject to such factors as flavor type and strength of flavor desired. Flavorants may be present in amounts up to about 4%, in one embodiment about 0.05% to about 3.0%, in another embodiment about 0.8% to about 2.5%, by weight of the total composition.

The present compositions may further comprise sweeteners. Suitable sweeteners include natural and artificial, water soluble, water insoluble and intense sweeteners. The sweetening agent may be dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, mannitol, xylitol, maltitol, isomalt, and hydrogenated starch hydrolysate or combinations thereof. Natural or artificial intense sweeteners such as dipeptide based intense sweeteners, monellin, thaumaoccous danielli, and L-aspartyl L-phenylalanine methyl ester and soluble saccharin salts may also be incorporated as sweeteners. The amount of the sweetener will vary with the type of sweetener selected and the desired level of sweetness. Sweetening agents and flavoring agents are typically used in oral care compositions at levels of from about 0.005% to about 5%, by weight of the composition.

Method of Preparation

In the above kits and compositions the polybutene component is suitably made as follows: polybutene is combined with any optional oral care active into a mixing vessel and mixed well with any means known within the art, for example, with spatula or mixer. Heat may be added to the composition during mixing. Continue mixing until homogenous. Where the oral care active is in solid particulate form, the addition of a viscosity modifier, such as silica, may be appropriate to keep the particulate dispersed and suspended within the composition. Flavorants and sweeteners are added as desired.

Where the oral care composition comprises an oral care carrier, the polybutene component is prepared as above. The oral care carrier, which may be a dentifrice, mouth rinse, mouth spray, or topical oral gel carrier is then added directly to the composition to create a single-phase oral care composition. Where it is desirable to deliver a multi-phase composition that is mixed at the time of application, the oral care carrier and the polybutene-containing component are physically separated until use.

The polybutene component of the oral care kits of the present invention is prepared as indicated above. In one oral care kit, a container, such as a jar, cup, can, tube, aerosol can, tub, pump, bottle or any other liquid holding or dispensing means, is filled with the polybutene composition. Sample accompanying instructions for the use of the kit would read: "Apply the oral care composition directly to the teeth. Apply a sufficient amount of the composition to coat the teeth directly to the teeth surfaces by finger, brush, dental stick, or cotton swab. It is not necessary to clean or dry the teeth either before or after application." In another oral care kit, the polybutene component is placed within any suitable applicator, such as a tube or pen applicator, for direct application to the teeth. Alternatively the polybutene component may be used in conjunction with a tray or stint serving as the applicator device. Where an applicator is included with the oral care kit of the present invention, sample instructions would read: "Apply the oral care composition directly to the teeth. Apply a sufficient amount to sufficiently coat the teeth by use of the enclosed applicator. It is not necessary to excessively clean, by brushing the teeth, or dry the teeth either before or after application." In another example, sample instructions may read: "Fill the supplied tray with an appropriate amount of the oral care composition. Insert tray into the oral cavity and fit directly on the teeth. It is not necessary to excessively clean, by brushing, or dry the teeth either before or after application."

Method of Use

The oral compositions of the present invention are in the form of toothpastes, dentifrices, topical oral gels, tooth whitening gels, mouth rinses, mouth sprays, and the like. The dentifrice compositions may be a paste, gel, or any configuration or combination thereof. If a multi-phase formulation is used, it is preferred that the dentifrice compositions be physically separated. In multi-phase formulations the form of components may differ. In one embodiment, for example, a dual-phase composition is comprised of one component in the form of a paste and another in the form of a gel. The dispenser may be a tube, pump, or any other container suitable for dispensing. Dual and/or multi compartment packages suitable for this purpose are described in U.S. Pat. Nos. 4,528,180; 4,687,663; and 4,849,213, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two or more separate dispensers, which are used to deliver two or more dentifrice compositions that are both used simultaneously.

In practicing the oral care kits and compositions of the present invention, the user applies the oral care compositions disclosed herein directly to the tooth surfaces. Where an applicator is included in the kit, the composition can be applied using the brush, pen applicator, doe's foot applicator, tray, stint or any other supplied application device known in the art. Where an applicator is not provided with the oral care kit or compositions of the present invention, the composition may also be applied by finger, cotton swab, or dental stick or the like. Where an oral care carrier is incorporated within the present invention, the composition is in the form of a dentifrice, toothpaste, mouth rinse, mouth spray, topical oral gel or whitening gel, the compositions are applied through traditional means. For example, toothpaste compositions are applied through brushing with a toothbrush; mouth rinse is applied by swishing the composition in the oral cavity and expectorating.

It is not necessary to prepare the oral cavity before applying the composition of the present invention. For example, the user may or may not choose to brush the teeth or rinse the mouth before applying the composition. The surfaces of the oral cavity are neither required to be dried nor to be excessively wet with saliva or water before the composition is applied. However, it is believed that adhesion to the tooth surfaces will be improved if the surfaces are drier when the composition is applied.

It should be understood that the present invention relates not only to oral care compositions for use on the teeth and hard surfaces of the oral cavity of a human, but also for use in the oral cavity of an animal, e.g. household pets or other domestic animals, or animals kept in captivity.

EXAMPLES

The following non-limiting examples further illustrate and describe the embodiments of the subject invention wherein both essential and optional ingredients are combined. It is to be understood that the examples are given solely for the purpose of illustration and are not to be construed as limiting the scope of the present invention, as many variations thereof are possible without departing from the spirit and scope of the invention.

The polybutene is combined with the oral care active (if included) into a mixing vessel and mixed well with a mechanical mixer. The composition is mixed until homogenous. Where the oral care active is in solid particulate form a viscosity modifier, such as silica, may be added to the mixture in the same manner and mixing continued until homogenous. Values given below are in weight percent of the polybutene component of the oral care kits and compositions of the present invention.

| Examples 1–6 | | | | | | |
|---|---|---|---|---|---|---|
| Ingredients | Ex. 1 | Ex. 2 | Ex. 3 | Ex. 4 | Ex. 5 | Ex. 6 |
| Polybutene[1] | 87% | 99.7% | 99.742% | 99.56% | 99.84% | 75.00% |
| Glass-H | | 13% | | | | 25.00% |
| Triclosan | | 0.3% | | | | |
| Thymol | | | | 0.064% | | |
| Eucalyptol | | | | 0.092% | | |
| Menthol | | | | 0.060% | 0.12% | |
| Methyl Salicylate | | | | 0.042% | | |
| Menthyl Lactate | | | | | 0.17% | |
| Peppermint | | | | | 0.15% | |
| 8-hydroxyquinoline salts | | | | | | 0.10% |
| $CuCl_2 \cdot 2H_2O$ | | | | | | 0.06% |

| Examples 7–12 | | | | | | |
|---|---|---|---|---|---|---|
| Ingredients | Ex. 7 | Ex. 8 | Ex. 9 | Ex. 10 | Ex. 11 | Ex. 12 |
| Polybutene[2] | 90% | 80% | 99.955% | 99.757% | 99.97% | 99.1% |
| CPC | | | 0.045% | | | 0.09% |
| Apple Extract | 10% | | | | | |
| Baking Soda | | 20% | | | | |
| Sodium Fluoride | | | | 0.243% | | |
| Nystatin | | | | | 0.03% | |

| Examples 13–19 | | | | | | | |
|---|---|---|---|---|---|---|---|
| Ingredients | Ex. 13 | Ex. 14 | Ex. 15 | Ex. 16 | Ex. 17 | Ex. 18 | Ex. 19 |
| Polybutene[3] | 90% | 90% | 90% | 99.76% | 99.76% | 99.76% | 99.066% |
| Carvacrol | 10% | | | | | | |
| Grape Seed Extract | | 10% | | | | | |
| Opatint D&C Red 27 | | | | 0.24% | | | |
| Red 7 | | | | | 0.24% | | |
| Red 30 | | | | | | 0.24% | |
| Grapefruit Seed Extract | | | 10% | | | | |
| Calcium Peroxide | | | | | | | 0.934% |

| Examples 20–25 | | | | | | |
|---|---|---|---|---|---|---|
| Ingredients | Ex. 20 | Ex. 21 | Ex. 22 | Ex. 23 | Ex. 24 | Ex. 25 |
| Polybutene[4] | | 90% | 99% | 99.47% | 97.95% | 99.24% | 92.5% |
| Xylitol | | 10% | | | | | |

-continued

| | | | | | |
|---|---|---|---|---|---|
| Chlorexidine | | 1% | | | |
| Stannous Fluoride | | | 0.53% | | |
| Tetra Sodium Pyrophosphate | | | | 2.05% | |
| Eugenol | | | | | 7.5% |
| Mono Fluoro Phosphate | | | | 0.76% | |

Examples 26–33

| Ingredients | Ex. 26 | Ex. 27 | Ex. 28 | Ex. 29 | Ex. 30 | Ex. 31 | Ex. 32 | Ex. 33 |
|---|---|---|---|---|---|---|---|---|
| Polybutene[5] | 81% | 81% | 81% | 80% | 56% | 80% | 81% | 100% |
| Sodium Percarbonate | 19% | | | 19% | 19% | | | |
| Urea Peroxide | | 19% | | | | | | |
| Calcium Peroxide | | | 19% | | | | | |
| Silica | | | | 1% | | | | |
| Petrolatum | | | | | 25% | | | |
| Benzocaine | | | | | | 20% | | |
| (Polyvinyl-Pyrrolidone) Peroxide Complex | | | | | | | 19% | |

Examples 34–37

| Ingredients | Ex. 34 | Ex. 35 | Ex. 36 | Ex. 37 |
|---|---|---|---|---|
| Polybutene[6] | 63.76% | 54.5% | 60.5% | 61.5% |
| Petrolatum | 10.00% | 12.5% | 12.5% | 12.5% |
| Silica | 1.00% | 1.0% | 1.0% | 1.0% |
| Glass-H | 25.00% | 25.0% | 25.0% | 25.0% |
| Peppermint Oil | | 6.0% | | |
| Asparatame | | 1.0% | 1.0% | |
| Opatint 27 | 0.24% | | | |

[1]Indopol H-300, MW = 1330, trade name of BP Amoco Chemicals (Chicago, IL).
[2]Indopol H-40, MW = 750, trade name of BP Amoco Chemicals (Chicago, IL).
[3]Indopol H-100, MW = 940, trade name of BP Amoco Chemicals (Chicago, IL).
[4]Indopol H-1900, MW = 2270, trade name of BP Amoco Chemicals (Chicago, IL).
[5]Indopol H-300, MW = 1330, trade name of BP Amoco Chemicals (Chicago, IL).
[6]Indopol H-300, MW = 1330, trade name of BP Amoco Chemicals (Chicago, IL).

It should be understood that the above-described polybutene-containing compositions may be combined in any ratio and used in the compositions and kits herein. It should also be understood that these examples are non-limiting. The level of polybutene and oral care actives exemplified herein may vary by as much as 80% and still be suitable for use in the compositions and kits disclosed herein.

Where the oral care composition optionally contain an oral care carrier the carriers are prepared by conventional means. Oral care carrier component #1 is prepared by conventional means. Mix sodium fluoride and saccharin in water. Disperse the xanthan gum in the sorbitol before adding to the mixture. Add the propylene glycol. Add flavorant, titanium dioxide and sodium alkyl sulfate. Add the silica. Continue mixing until homogenous. Mill and/or deareate the final product if desired for aesthetic preference.

Oral care carrier component #2 is prepared by conventional means. Mix sodium fluoride and saccharin in water in a mixing vessel. Disperse the thickening agents, carboxymethylcellulose and xanthan gum in the glycerin before adding to the mixture. Add the propylene glycol. Add flavorant, titanium dioxide and sodium alkyl sulfate. Add the sodium carbonate. Add the silica and then the sodium bicarbonate. Slowly add the tetrasodium pyrophosphate and then the calcium peroxide. Continue mixing until homogenous. Mill and/or deareate the final product if desired for aesthetic preference.

Oral care carrier component #3 is prepared by conventional means. sodium fluoride, saccharin and water to a mixing vessel. Disperse the thickeners, carboxymethylcellulose, in the glycerin and sorbitol before adding to the mixture. Add the propylene glycol, flavorant, titanium dioxide and sodium alkyl sulfate. Next add the sodium carbonate, silica and sodium bicarbonate. Continue mixing until homogenous. Mill and/or deareate the final product if desired for aesthetic preference.

| Ingredient | Oral Care Carrier Component #1 | Oral Care Carrier Component #2 | Oral Care Carrier Component #3 |
|---|---|---|---|
| Sodium Fluoride | 0.24% | 0.24% | 0.24% |
| Water | 12.00% | 15.00% | 10.00% |
| Flavorant | 1.00% | 1.00% | 1.00% |
| Sorbitol | 58.36% | | 25.06% |
| Titanium Dioxide | 0.50% | 1.00% | 0.50% |
| Xanthan Gum | 0.50% | 0.20% | |
| Sodium Alkyl Sulfate | 4.00% | 4.00% | 4.00% |
| Silica | 20.00% | 22.00% | 15.00% |
| Polyethylene Glycol | 3.00% | 3.00% | 3.00% |
| Sodium Saccharin | 0.40% | 0.40% | 0.40% |
| Carboxymethyl-cellulose | | 0.90% | 0.80% |
| Glycerin | | 24.76% | 8.00% |
| Calcium Peroxide | | 1.00% | |
| Sodium Carbonate | | 2.00% | 2.00% |
| Sodium Bicarbonate | | 14.50% | 30.00% |
| Tetrasodium Pyrophosphate | | 10.00% | |

The two components can be physically separated until administration to the teeth and hard, fixed surfaces of the oral cavity by the use of a dual chamber dentifrice dispenser. Alternatively the polybutene component and the oral care carrier component can be combined and packaged as a single-phase oral care composition. Where a single phase composition is desired it may be necessary to emulsify the polybutene component with the oral care carrier component of the oral care composition.

It is understood that the examples and embodiments described herein are for illustrative purposes only and that various modifications or changes in light thereof will be suggested to one of skill in the art without departing from the scope of the present invention.

What is claimed is:

1. A non-mucoadhesive oral care composition comprising:
   (a) polybutene having a number average molecular weight of about 300 to about 3000;
   (b) at least one carrier which is safe and effective for use in an oral care composition; and
   (c) an effective amount of a flavoring agent and/or sweetener;
   wherein said composition is not self-supporting and is not a chewing gum.

2. The oral care composition according to claim 1 wherein the polybutene has a molecular weight of about 500 to about 2200.

3. The oral care composition according to claim 2 wherein the polybutene has a molecular weight of about 750 to about 1500.

4. The oral care composition according to claim 1 wherein the carrier is selected from the group consisting of; abrasive polishing materials; buffering agents; water; surfactants; pigments; colorants; dyes, and lakes; thickening agents; opacifiers; humectants; xylitol; and mixtures thereof.

5. The oral care composition according to claim 1 wherein the composition is in the form of a single or multi phase toothpaste, dentifrice, topical oral gel, tooth whitening gel, mouth rinse, or mouth spray.

6. A non-mucoadhesive oral care composition comprising:
   (a) polybutene having a number average molecular weight of about 300 to about 3000;
   (b) an effective amount of an oral care active agent;
   (c) at least one carrier which is safe and effective for use in an oral care composition; and
   (d) an effective amount of a flavoring agent and/or sweetener;
   wherein said composition is not self-supporting and is not a chewing gum.

7. The oral care composition according to claim 6 wherein the oral care active is selected from the group consisting of anti-calculus agents; fluoride ion sources; stannous ion sources; whitening agents; anti-microbial and anti-plaque agents; anti-inflammatory agents; nutrients; antioxidants; anti-viral agents; anti-fungal agents; analgesic and anesthetic agents; H-2 antagonists; components other than polybutene which impart a clean feel to the teeth; fragrances and sensates; and mixtures thereof.

8. The oral care composition according to claim 7 wherein the oral care active is selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, Opatint D&C Red 27, polyphosphates, and cetylpyridium chloride.

9. The oral care composition according to claim 8 wherein the polyphosphate is sodium hexametaphosphate.

10. The oral composition care according to claim 6 wherein the oral care carrier is selected from the group consisting of abrasive polishing materials, buffering agents, water, surfactans, thickening agents, opacifiers, humectants, xylitol and mixtures thereof.

11. The oral care composition according to claim 10, wherein the composition is in the form of a single or multi phase toothpaste, dentifrice, topical oral gel, tooth whitening gel, mouth rinse, or mouth spray.

12. The oral care composition according to claim 6 wherein the oral care composition further comprises a viscosity modifier.

13. The oral care composition according to claim 6 wherein the polybutene has a molecular weight of about 500 to about 2200.

14. The oral care composition according to claim 13 wherein the polybutene has a molecular weight of about 750 to about 1500.

15. An oral care kit comprising a non-mucoadhesive oral care composition, said composition comprising:
   (a) polybutene having a number average molecular weight of about 300 to about 3000;
   (b) at least one carrier which is safe and effective for use in an oral care composition;
   (c) an effective amount of a flavoring agent and/or sweetener; and
   (d) a container;
   wherein the kit does not contain a dental care strip, and said composition is not self-supporting and is not a chewing gum.

16. The oral care kit according to claim 15 wherein the polybutene has a molecular weight of about 500 to about 2200.

17. The oral care kit according to claim 16 wherein the polybutene has a molecular weight of about 750 to about 1500.

18. The oral care kit according to claim 15 wherein said composition further comprises at least one oral care active.

19. The oral care kit according to claim 18 wherein the oral care active is selected from the group consisting of anti-calculus agents; fluoride ion sources; stannous ion sources; whitening agents; anti-microbial and anti-plaque agents; anti-inflammatory agents; nutrients; antioxidants; anti-viral agents; anti-fungal agents; analgesic and anesthetic agents; H-2 antagonists; components other than polybutene which impart a clean feel to the teeth; fragrances and sensates; and mixtures thereof.

20. The oral care kit according to claim 19 wherein the oral care active is selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, Opatint D&C Red 27, polyphosphates, and cetylpyridium chloride.

21. The oral care kit according to claim 20 wherein the polyphosphate is sodium hexametaphosphate.

22. The oral care kit according to claim 18 wherein the composition further comprises a viscosity modifier.

23. An oral care kit comprising a non-mucoadhesive oral care composition, said composition comprising:
   (a) polybutene having a number average molecular weight of about 300 to about 3000;
   (b) at least one carrier which is safe and effective for use in an oral care composition;
   (c) an effective amount of a flavoring agent and/or sweetener; and
   (d) an applicator for applying said polybutene to teeth;
   wherein the kit does not contain a dental care strip, and said composition is not self-supporting and is not a chewing gum.

24. The oral care kit according to claim 23 wherein the polybutene has a molecular weight of about 500 to about 2200.

25. The oral care kit according to claim 24 wherein the polybutene has a molecular weight of about 750 to about 1500.

26. The oral care kit according to claim 23 wherein said composition further comprises at least one oral care active.

27. The oral care kit according to claim 26 wherein the oral care active is selected from the group consisting of anti-calculus agents, fluoride ion sources, stannous ion sources, whitening agents, anti-microbial and anti-plaque agents, anti-inflammatory agents, nutrients, antioxidants, anti-viral agents, anti-fungal agents, analgesic and anesthetic agents, H-2 antagonists, components other than polybutene which deliver a clean feel to the teeth, fragrances and sensates, pigments and colorants, and mixtures thereof.

28. The oral care kit according to claim 27 wherein the oral care active is selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, Opatint D&C Red 27, polyphosphates, and cetylpyridium chloride.

29. The oral care kit according to claim 28 wherein the polyphosphate is sodium hexametaphosphate.

30. The oral care kit according to claim 29 wherein the composition further comprises a viscosity modifier.

31. A method of coating teeth comprising applying, to the teeth of a subject in need thereof, a non-mucoadhesive oral care composition comprising:
 (a) polybutene having a number average molecular weight of about 300 to about 3000;
 (b) at least one carrier which is safe and effective for use in an oral care composition; and
 (c) an effective amount of a flavoring agent and/or sweetener;
 wherein said composition is not self-supporting and is not a chewing gum.

32. A method of providing sustained release of therapeutic and/or cosmetic actives to an oral cavity comprising applying, to the oral cavity of an individual in need thereof, a non-mucoadhesive oral care composition comprising:
 (a) polybutene having a number average molecular weight of about 300 to about 3000;
 (b) at least one carrier which is safe and effective for use in an oral care composition; and
 (c) an effective amount of a flavoring agent and/or sweetener;
 wherein said composition is not self-supporting and is not a chewing gum.

33. A method of inhibiting gingivitis, caries, staining, fungi, bacteria and/or plaque build up in an oral cavity comprising applying, to the oral cavity of an individual in need thereof, a non-mucoadhesive oral care composition comprising:
 (a) polybutene having a number average molecular weight of about 300 to about 3000;
 (b) at least one carrier which is safe and effective for use in an oral care composition; and
 (c) an effective amount of a flavoring agent and/or sweetener;
 wherein said composition is not self-supporting and is not a chewing gum.

34. A method of imparting a clean feel to teeth comprising applying, to the teeth of individual in need thereof, a non-mucoadhesive oral care composition comprising:
 (a) polybutene having a number average molecular weight of about 300 to about 3000;
 (b) at least one carrier which is safe and effective for use in an oral care composition; and
 (c) an effective amount of a flavoring agent and/or sweetener;
 wherein said composition is not self-supporting and is not a chewing gum.

* * * * *